United States Patent
Fleming

(10) Patent No.: US 9,566,037 B2
(45) Date of Patent: Feb. 14, 2017

(54) FLEMING METHOD FOR TISSUE AND VASCULAR DIFFERENTIATION AND METABOLISM (FMTVDM) USING SAME STATE SINGLE OR SEQUENTIAL QUANTIFICATION COMPARISONS

(71) Applicant: Richard Max Fleming, Studio City, CA (US)

(72) Inventor: Richard Max Fleming, Studio City, CA (US)

( * ) Notice: Subject to any disclaimer, the term of this patent is extended or adjusted under 35 U.S.C. 154(b) by 732 days.

(21) Appl. No.: 13/986,869

(22) Filed: Jun. 13, 2013

(65) Prior Publication Data

US 2014/0371579 A1 Dec. 18, 2014
US 2016/0374634 A9 Dec. 29, 2016

Related U.S. Application Data

(60) Provisional application No. 61/658,428, filed on Jun. 12, 2012.

(51) Int. Cl.
A61B 5/1455 (2006.01)
A61B 6/00 (2006.01)
A61B 6/03 (2006.01)

(52) U.S. Cl.
CPC ............... *A61B 6/503* (2013.01); *A61B 6/037* (2013.01); *A61B 6/486* (2013.01); *A61B 6/5217* (2013.01)

(58) Field of Classification Search
CPC .................................................... A61B 6/503
See application file for complete search history.

(56) References Cited

PUBLICATIONS

Fleming-Harrington Redistriution Wash-in washout (FHRWW) :The platinum Standard for nuclear cardiology, p. 207-250, 2011.*

* cited by examiner

*Primary Examiner* — Joseph M Santos Rodriguez

(57) ABSTRACT

The present invention defines the parameters whereby "quantification" of isotope emission may occur and be clinically applied and provides a method for detecting abnormal coronary blood flow by "quantifying" emissions of a radiopharmaceutical after stressing the heart either pharmacologically or physiologically under "same state" conditions of stress-stress for detection of ischemic vascular (IVD) disease and the ability to differentiate (a) ischemic heart disease (IHD) due to narrowed coronary lumen and subsequent reduced lumen responsiveness to demand for more coronary blood flow and (b) vulnerable inflammatory plaque (VIP) disease, which reduces lumen responsiveness to blood flow demand with potential for sudden rupture and sudden cardiac death. The present invention also provides a method of detection of myocyte viability by using the "quantitative" method to differentiate "normal" functioning cardiac tissue from non-viable "infarcted" cardiac tissue and from "stunned/hibernating" myocytes, which may benefit from intervention. The present invention further provides a method for detection of IVD by detecting enhanced thymic activity associated with IVD and treatable causes. The present invention does so while reducing total patient imaging time, patient table time, radiation isotope doses and exposure to both patient and others through primary and secondary exposure to isotope emissions. In one embodiment, the nuclear isotope is technetium-99m hexakis 2-methoxyisobutylisonitrile (sestamibi).

1 Claim, 17 Drawing Sheets

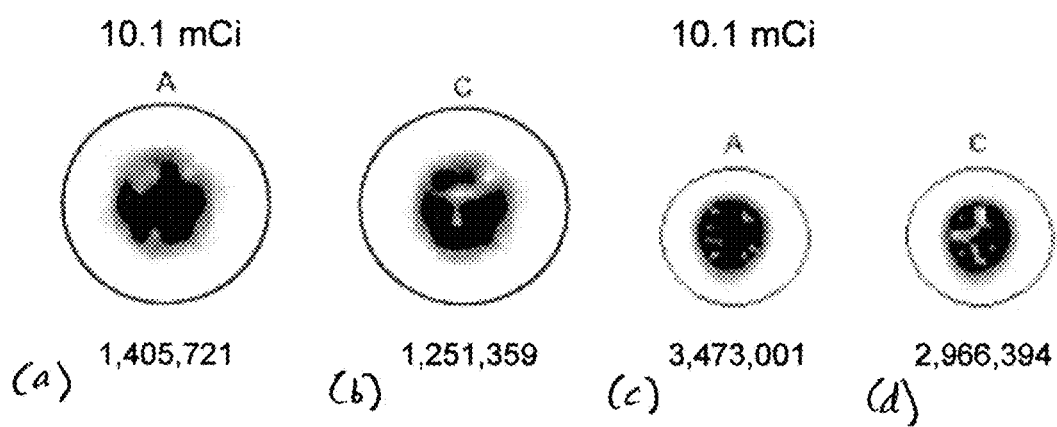
Figure 2. Changes in isotope counts using 64 x 64 (a, b) and 128 x 128 matrix (c, d).

Figure 3. Changes in counts over time.
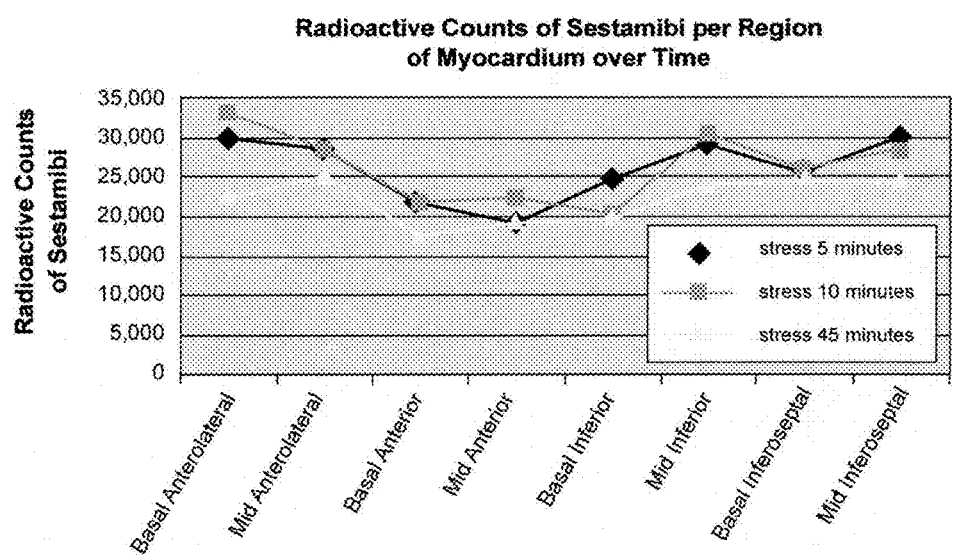

Figure 4. Protocols.
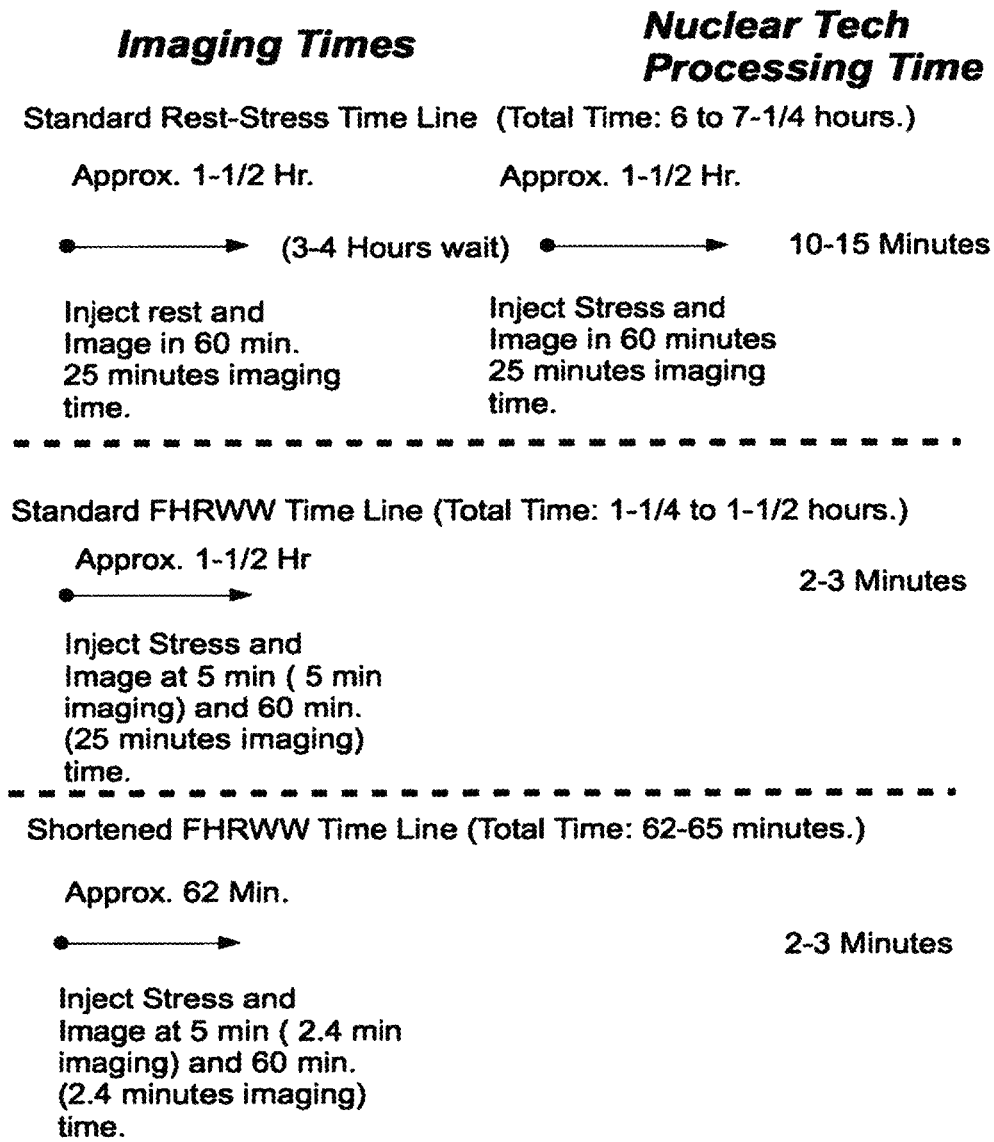

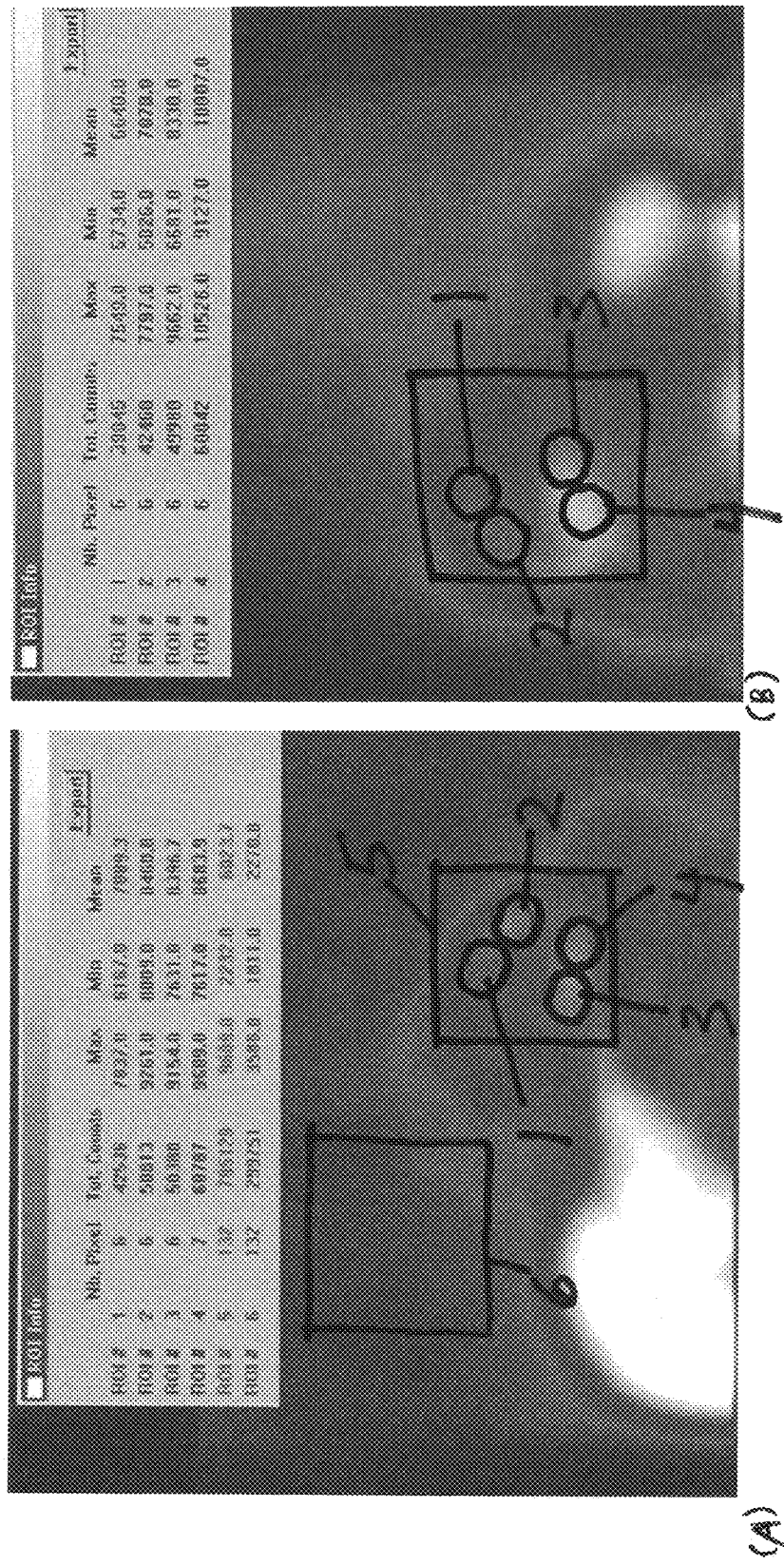
Figure 5. Images at 5 minutes and 60 minutes

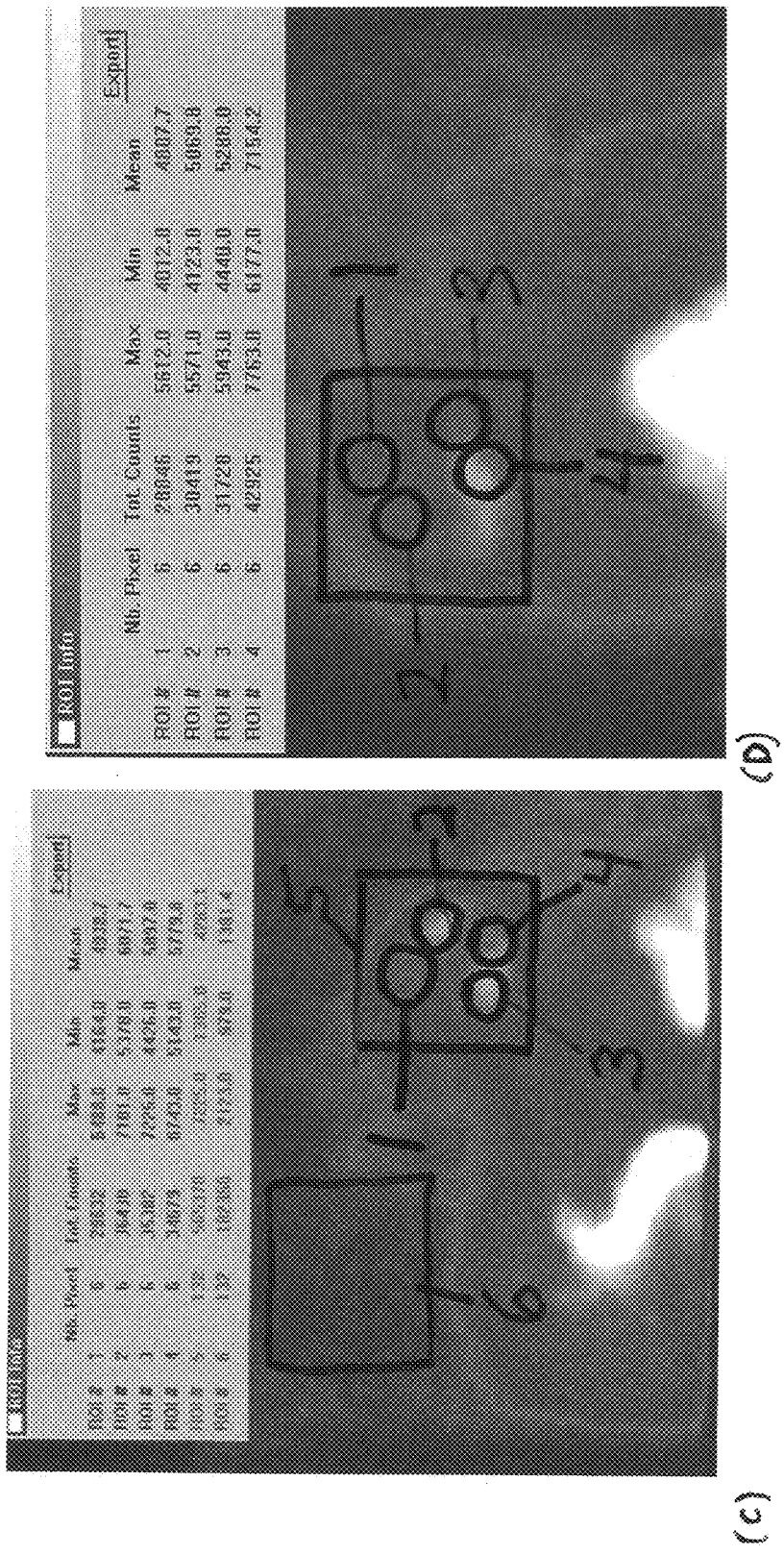
Figure 5. Images at 5 minutes (A,B) and 60 minutes (C,D)

Series 2 is 5-minutes and series 1 is 60-minutes.

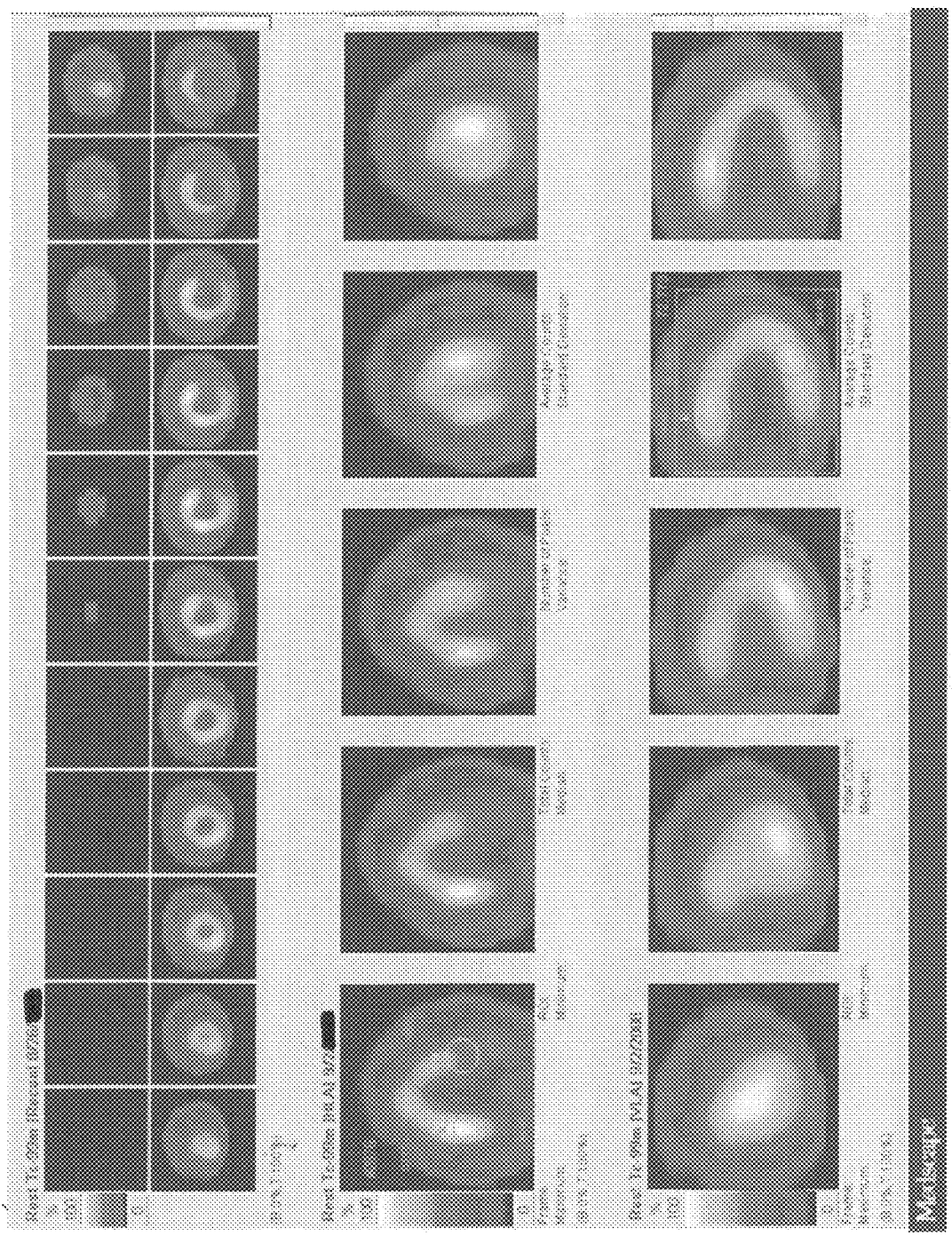

Figure 9(b). Changes in resting counts.
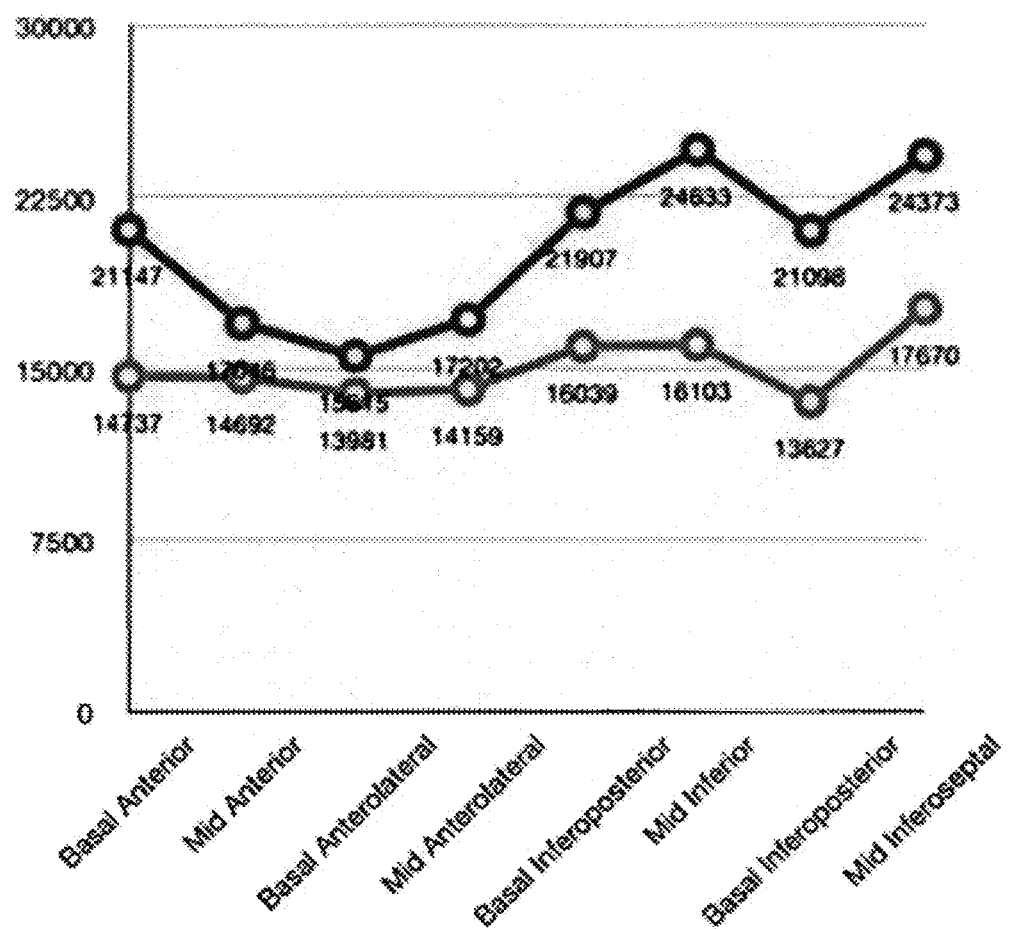

Figure 10. Cardiac images.
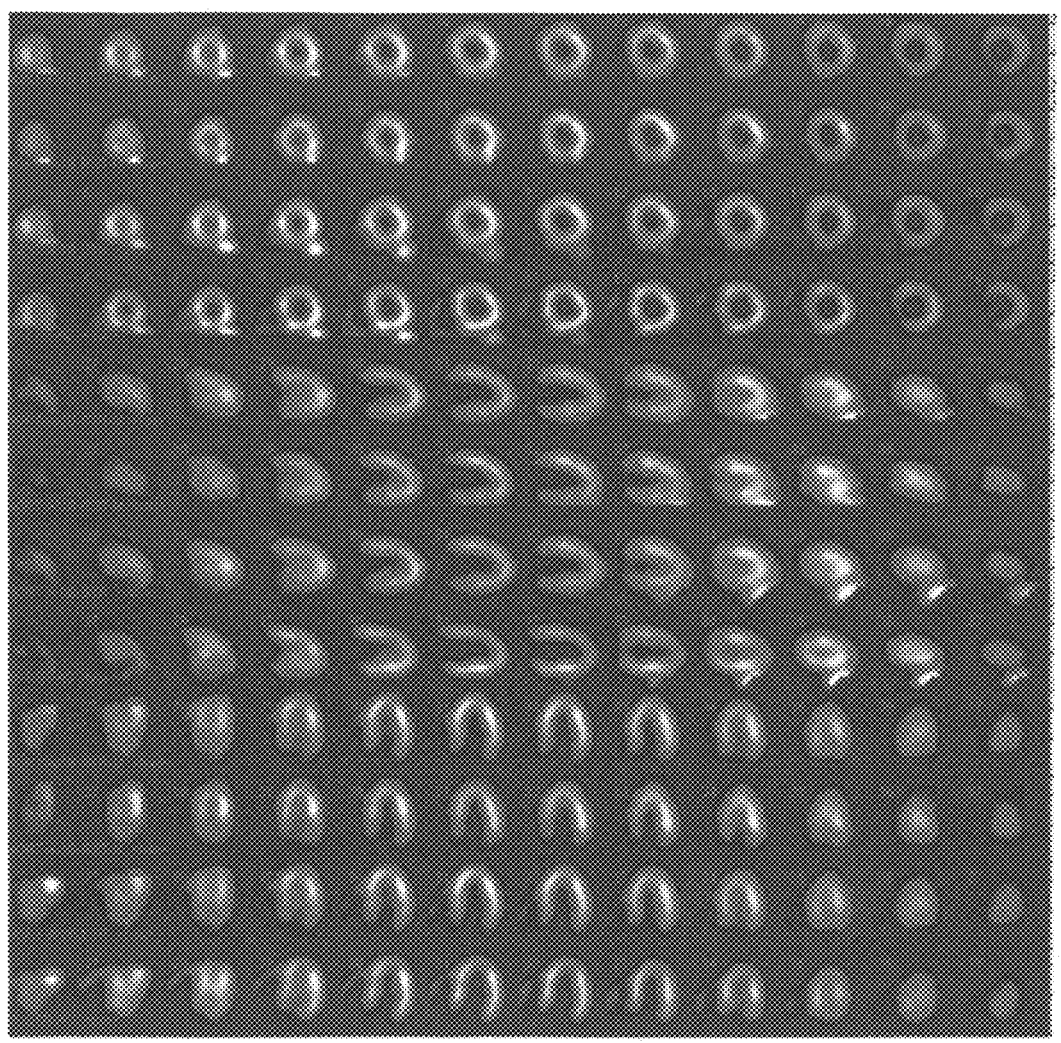

Figure 12(B) FMTVDM
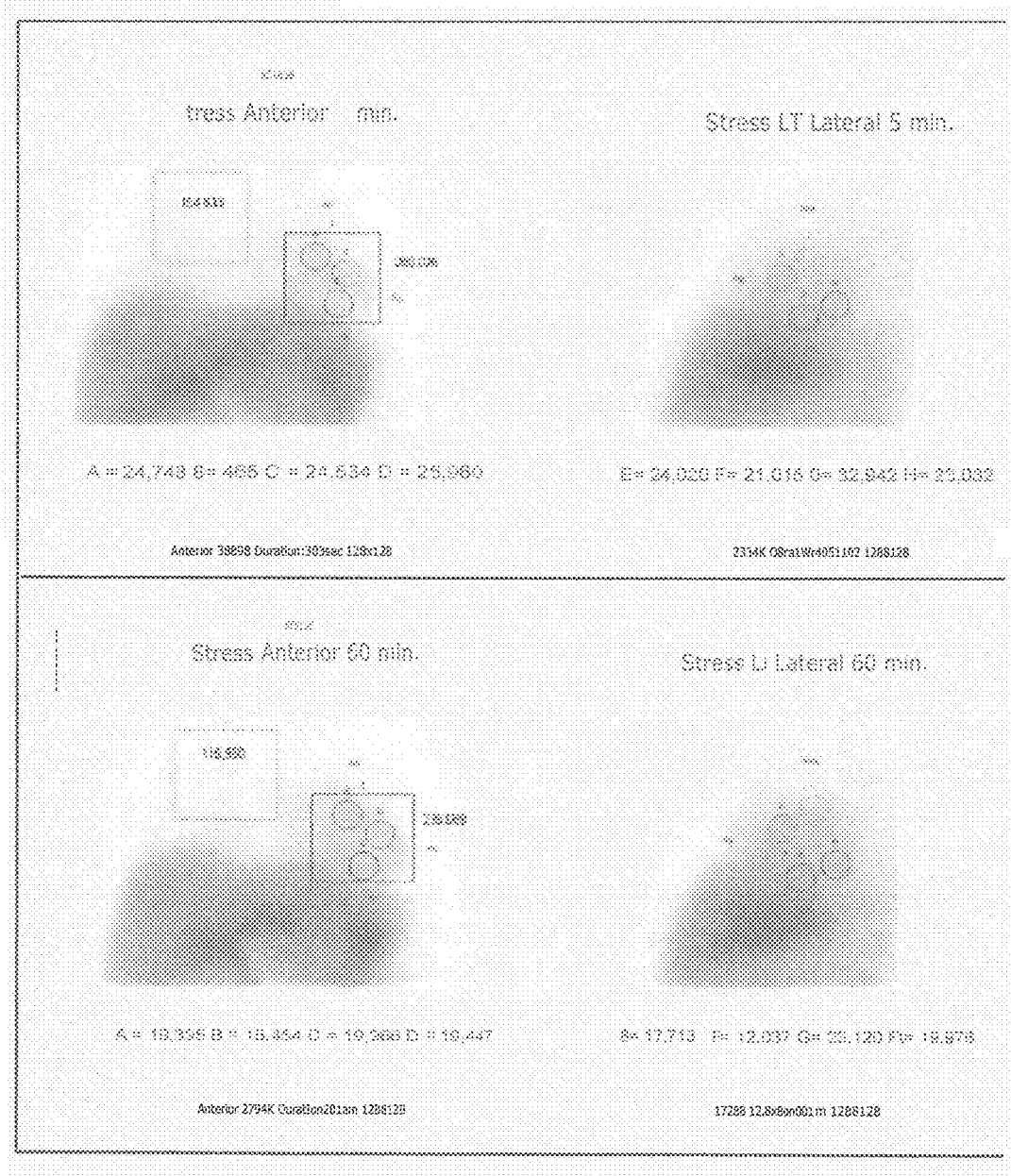

FLEMING METHOD FOR TISSUE AND VASCULAR DIFFERENTIATION AND METABOLISM (FMTVDM) USING SAME STATE SINGLE OR SEQUENTIAL QUANTIFICATION COMPARISONS

FIELD OF THE INVENTION

The present invention relates to methods for (a) detecting "Inflammation and Vascular Disease" (© TX 7-451-244) (IVD) including but not limited to ischemic coronary artery disease (IHD) and vulnerable inflammatory plaque (VIP) disease and (b) tissue viability differentiating "normal" myocardium from "stunned/hibernating" or "infarcted" myocardium, using "quantitative" comparisons of tissue under same state conditions. The present invention also relates to a method for differentiation tissue damage and differentiating between "normal" tissue, dead/necrotic tissue (infarction) and that which has been injured sufficiently to impair function (stunned/hibernating), yet is presently recoverable. Finally, the present invention provides a method for further detection of IVD by demonstrating increased uptake of the isotopes by the thymus gland, with evidence of increased thymus gland enlargement and elevations in hs-CRP.

BACKGROUND OF THE INVENTION

Conventional nuclear cardiac imaging performed with either planar, single photon emission computed tomography (SPECT) or positron emission tomography (PET) camera and computer detection systems currently utilizes comparison of "rest" and "stress" imaging for comparisons to determine the presence or absence of ischemia and infarcted tissue. Acquisition of cardiac images using these cameras and nuclear isotopes under either stress or resting conditions are defined as nuclear cardiac studies (NCS).

By convention, patients may have either the "stress" study or "rest" study done first. When there is no abnormality seen on either study, the patient is reported to be "normal." When the "stress" image is abnormal and the "rest" image is normal, the interpretation is that of ischemia. When both "stress" and "rest" images are abnormal (in the same region of the heart), the interpretation is no ischemia but infarction.

Currently, there are more than 11 million nuclear cardiac studies performed in the U.S. yearly with a 35% error rate. This error rate however does not take into account errors made where the area of the heart is incorrect (e.g. ischemia reported in the area of the right coronary artery with angiographic analysis showing it is the left anterior descending artery). These studies are considered correct "for detection of ischemia" even though the area of the heart involved is incorrect. Of the 35% known errors, approximately 70,000 to 90,000 individuals are told they do not have ischemic heart disease (MD) only to go home and die soon thereafter from IVD and myocardial infarction (MI).

The first nuclear cardiac studies (NCS) looking for coronary artery disease (CAD) were introduced in the 1970's and employed exercise stress to increase the demand for coronary blood flow and detect IHI) thought to be due to narrowing of one or more coronary arteries (Stenosis Flow Reserve/SFR© TX 7-451-241). Following the use of exercise or pharmacologic stress, Thallium-201 (Tl-201) was injected through an intravenous catheter and one hour later "stress" images were taken followed three to four hours by the acquisition of "redistribution" images. The images "stress-redistribution" were then compared using the method described supra to make a determination of ischemia and/or infarction.

With the introduction of Technetium-99m hexakis 2-methoxyisobutylisonitrile (sestamibi) in the late 1980's, the pharmaceutical company owning sestamibi then and now, recommend that two separate injections of the isotope be given, one at "stress" and another at "rest." This recommendation was based upon the premise that sestamibi did not redistribute like T1-201. These studies are plagued by the same 35% error rate noted supra.

In 2001 we noticed, while developing Breast Enhanced Scintigraphy Test (B.E.S.T.©) Imaging, that imaging of the heart performed five minutes (FIG. 1) after the injection of sestamibi following either physiologic stress using a pharmacologic agent or using exercise stress, showed a different result than images taken sixty minutes after the isotope was injected. Conventional thinking was that sestamibi did not redistribute and if it did Crane showed this occurred 28 minutes after injection; NOT earlier. However, the five-minute images demonstrated not only that sestamibi redistributes, but also that it is this initial "early" five-minute acquisition that was crucial to differentiating IVD. While Crane reported that sestamibi washout could occur after 28 minutes under ischemic conditions, there is no report indicating this could occur earlier or would be diagnostically useful. Crane shows no five minutes post injection characteristics indicating the usefulness of imaging at five-minutes and there is no report other than our work, which looks at the clinical importance of looking at the differences between five and sixty minute image analysis and it's ramifications on the detection of IVD. Specifically, Crane was not defining "redistribution", only that the isotope left tissue earlier than expected; viz. at 28 minutes. The term "redistribution" (other than our work) of sestamibi employed in the literature to date talks about changes between "stress" and "rest" sestamibi images and NOT the phenomena we have noted between five and sixty-minute "stress" images.

Additionally, we noted prominent uptake of sestamibi by the thymus gland (see FIG. 1b), which is detectable only during the first ten-minutes following injection of the isotope following pharmacologic or physiologic stress. Images taken later than this ten-minute interval showed no significant detectability of the thymus gland. Results showed IVD and elevated markers of IVD, specifically hs-CRP associated with thymus uptake and detectability. Successful treatment of the IVD demonstrated an absence of thymus detectability using this method, a normalization of the hs-CRP level and improvement in subsequent IVD.

Since SFR© as we have defined it, is the difference between peak blood flow and least blood flow under physiologic demand, not implied to be resting flow, the detection of IVD requires a comparison of same state conditions for correct interpretation of diagnosis of IVD, including IHD and VIP disease. This same state condition is "stress"-"stress."

Comparison of same state "stress"-"stress" image comparisons using five and sixty-minute images acquired by NCS can be visually (qualitatively) noted to be different in individuals with IVD. This is determined "quantitatively" by comparing identical regions of interest (ROIs) from the five-minute image(s) with the sixty-minutes image(s). When there is no IVD, the "quantified" counts per ROI are the same as that seen at sixty-minutes, correcting for isotope decay (appendix A). While this varies depending upon the isotope used and the actual time between the two sets of images, taken post-stress, a mathematical model (viz.

FHRWW©) compares the "quantified" counts in the ROIs between the two sets of images (appendix A). When VIP is present by intravascular (IVUS) ultrasound and/or angiographic results, little impairment in coronary blood flow is seen within the lumen of the artery. Under these conditions, the major limitation is the ability of the artery to dilate and augment coronary flow to peak levels and a diminished SFR© is seen. These individuals take longer for the isotope to accumulate in that region of the heart compared with regions with normal blood flow. As a result, the initial five-minute counts are less than the later sixty-minute counts. This is defined as "wash-in" and reflects a significant number of individuals whose IVD is missed by "rest-stress" imaging where only a sixty-minute post stress image is obtained, when the isotope has had sufficient time to "wash-in."

When IVD is associated with coronary lumen narrowing, the initial five-minute counts per ROI are greater than that present in the same ROI at sixty-minutes after correction for isotope decay (defined in appendix A). Under these conditions, "washout" of the isotope is seen, but in fact, this "washout" or loss of isotope above expected decay of the isotope, is associated with MD. Unlike the errors seen in "rest-stress" imaging, "stress-stress" FHRWW © correctly identifies the diseased artery, as confirmed by coronary angiography.

When IVD is absent and coronary blood flow is not impaired, comparison of identical ROIs from the five-minute and sixty-minute images, reveal similar isotope counts, corrected for isotope decay (appendix A). Given the information obtained from "wash-in" "washout" this represents a state where the isotope is constantly being delivered to myocytes, taken up by the cells, released from the cells, retaken up by the cells, repeating the process during isotope decay.

Multiple methods have been studied to determine if impaired myocyte function is the result of MI or whether there is stunned or hibernating myocardium present. Stunned or hibernating myocardium reflects damaged/injured cardiac tissue, which is not demonstrating contractile or other grossly detectable cellular function. However, under these conditions, the cells have been "temporarily" damaged and with sufficient recovery of blood flow, my return to normal function. Stunned myocardium represents a state where the effect is of less duration than that noted in hibernating myocardium. These other methods have not demonstrated clinical utility and most if not all of them have subsequently been abandoned.

Similarly, the detection of cardiac IVD, tissue viability requires a comparison of same state conditions; but under "rest"–"rest" conditions. "Rest"-"rest" compares myocyte ability to "redistribute" the isotope being imaged by the nuclear camera without the introduction of pharmacologic or physiologic stress.

As with "stress"-"stress" detection of IVD, the comparison of same state "rest" "rest" ROIs can be used to determine tissue viability (FHRWW©). When the five and sixty-minute counts for ROIs are compared, they yield cardiac tissue viability when compared with electrocardiogram, enzymatic and echocardiographic results. Here when the five and sixty-minute counts per ROI are essentially the same after correction for isotope decay, cardiac tissue is "normal" and functional.

When the cardiac tissue in infarcted, both the five-minute ROI counts are lower than the "normal" myocardium, with little if any change between the counts at five and sixty minutes. Stunned/hibernating myocardium initially has ROI counts greater than the infarcted tissue but less than the "normal" myocardium.

Efforts to improve "qualitative" image comparison have resulted in nuclear camera companies increasing the number of pixels for visual resolution. These results give a visually pleasing appearance; however, there is no published data as to the "quantitative" reliability of these images. Since FHRWW© "quantification" requires accurate statistical counts, we looked at the ability of different settings to produce different results. Importantly diagnostic capabilities for these absolute measurements are not human limited, but rather, are the consequential results of modulation transfer function (MTF) as demonstrated in FIG. 2. Using known isotope decay data as the absolute determination of changes in radiation count detection by nuclear cameras, their hardware and software, we demonstrated using sealed sources of Technetium 99-m (Tc-99m) that MTF is greater for a 64×64 matrix with a count reduction of 11% over fifty-five minutes for sestamibi isotope decay. The 128×128 matrix, while providing a more visually appealing picture for "qualitative" image comparison, was associated with an almost 50% loss of data, yielding inaccurate diagnostic results.

SUMMARY OF THE INVENTION

The present invention provides a "quantitative" method for differentiating IVD through the "quantitative" comparison of ROIs under same state conditions, following pharmacologic or physiologic stress. Furthermore, it allows the differentiation between the more critically diseased VIPs and the conventionally considered IHD. Such differentiation is critical for treatment response and dramatically reduces cardiac death. Under same state "rest"-"rest" conditions, the method can be employed to differentiate "normal" myocytes from infarcted tissue, while detecting the presence of "stunned/hibernating" tissue, which would benefit from intervention while "infarcted" tissue will not. Further, this ability to "quantitate" these differences is contingent upon using the right settings to establish correct MTF and avoid loss of data, which occurs through methods, which enhance visual appearance at the loss of validity.

In one embodiment of the present invention, sestamibi is used as the isotope to be "quantified" using high-dose dipyridamole (HDD) at 0.852 mg/kg body weight of the patient to optimize changes in coronary flow.

While the present invention has been tested in coronary arteries and described in connection with IVD and differentiation of myocyte viability, the principles are equally applicable to other organs and determination of limitations in their blood flow and tissue viability. The present invention also does not limit the timing of the images (FIG. 3), with the images of greatest importance appearing to be the earlier five-minute images for detection of "wash-in.". Additionally, the amount of time required for image acquisition is dependent upon the camera, hardware, computer system and software and the amount of table time (time a patient spends lying on the table for image acquisition) does not alter the principles of this invention.

BRIEF DESCRIPTION OF THE DRAWINGS

FIG. 2 shows the effect of modulation transfer factor (MTF) diminishing accuracy of isotope "quantification" when matrix changes from 64×64 to 128×128.

FIG. 3 shows the difference in counts for ROIs over time to determine the optimum timing for image acquisition using a 64×64 matrix.

FIG. 4 shows the protocols used for nuclear cardiac studies (NCS) including the currently employed "standard" protocol, which can be and is performed using either a "rest-stress" sequence or "stress-rest" sequence. FHRWW© protocols/methods are shown using two different nuclear camera systems which comprises different "table time."

FIG. 5 shows nuclear images of the heart under "same state" conditions of "stress-stress."

FIG. 9 shows the results of "rest-rest" viability analysis using FHRWW© to determine if the tissue is "normal", "stunned/hibernating" or "infarcted." Panel (a) shows actual images, while panel (b) shows the graphic comparison required by the present invention to make the diagnosis of tissue viability.

FIG. 10 shows the results of "stress-rest" imaging in a patient using both the standard approach and attenuation correction designed to correct for artifacts. The images show no significant IVD and were interpreted that way.

DETAILED DESCRIPTION OF A PREFERRED EMBODIMENT

Figure 1:
FIG. 1a shows a five-minute post stress image demonstrating photopenia in the anterior wall of the heart as seen on the central panel.
FIG. 1b shows a five-minute post stress image demonstrating increase uptake of sestamibi by the thymus gland associated with IVD and elevated hs-CRP levels.

The present invention provides an improved method for the detection of IVD. In one method of the present invention the comparison of same state "stress-stress" images, acquired at five and sixty-minutes post pharmacologic or physiologic stress allows for the "quantitative" differentiation between ischemic coronary artery disease (IHD) produced by lumen narrowing and vulnerable inflammatory plaques (VIPs) associated with extension of the arterial wall, impairing stenosis flow reserve©.

The sequence of pharmacologic and/or physiologic stress utilized to investigate the presence or absence of coronary artery disease (CAD) follows the methods laid out in Fleming R M. Chapter 31. Nuclear Cardiology: Its Role in the Detection and Management of Coronary Artery Disease. *Textbook of Angiology*. John C. Chang Editor, Springer-Verlag New York, N.Y. 1999, pp. 397-406; Fleming R M, Detecting Coronary Artery Disease Using SPECT Imaging: A Comparison of Thallium-201 and Teboroxime. Am J Physiol Imag 1992; 7(1):20-23; Fleming R M, Rose C H, Feldmann K M. Comparing a High Dose Dipyridamole SPECT Imaging Protocol with Dobutamine and Exercise Stress Testing Protocols. Angiology 1995; 46(7):547-556; Fleming R M, Feldmann K M. Comparing a High Dose Dipyridamole SPECT Imaging Protocol with Dobutamine and Exercise Stress Testing Protocols. Part II: Using High-Dose Dipyridamole to Determine Lung-to-Heart Ratios. Intern J Angiol 1998; 7:325-328; the disclosure of which is incorporated herein by this reference. The camera device used for these studies include but are not limited to planar devices, single photon emission computed tomography (SPECT), positron emission tomography (PET), hand held detectors, semiconductors, or other suitable devices capable of "quantifying" isotope emissions.

Following "stress", 25-30 mCi sestamibi is introduced through the intravenous (IV) catheter and the IV flushed with 10-20 cc of normal saline to assure that the entire isotope has been introduced into the patient. Resting images for sestamibi "rest" imaging is performed using the standard method describe by Fleming in Fleming R M. Chapter 31. Nuclear Cardiology: Its Role in the Detection and Management of Coronary Artery Disease. *Textbook of Angiology*. John C. Chang Editor, Springer-Verlag New York, N.Y. 1999, pp. 397-406, the disclosure of which is incorporated herein by this reference.

Acquisition of the first set of post-stress cardiac images are initiated five-minutes after introduction of sestamibi into the patients venous system as shown in FIG. 4. A second set of images is acquired at sixty-minutes post isotope injection, matching the acquisition of the two sets of images either by external or internal markers of position. As shown in FIG. 4, the amount of time required to acquire these images will be camera dependent and the principles of this invention are applicable independent of the amount of time required by a specific camera.

The nuclear technologist then processes and reconstructs the images per standard approach by the camera software and when available (although not required for the present invention) attenuation correction is applied using available manufacturer software as described in Fleming R M. Chapter 31. Nuclear Cardiology: Its Role in the Detection and Management of Coronary Artery Disease. *Textbook of Angiology*. John C. Chang Editor, Springer-Verlag New York, N.Y. 1999, pp. 397-406, the disclosure of which is incorporated herein by this reference. An example of this is shown in FIG. 10. Following this, cardiac images are displayed and matched to regions of interest (ROIs) identified either by computer software, personnel or a combination of the two.

Figure 12A:
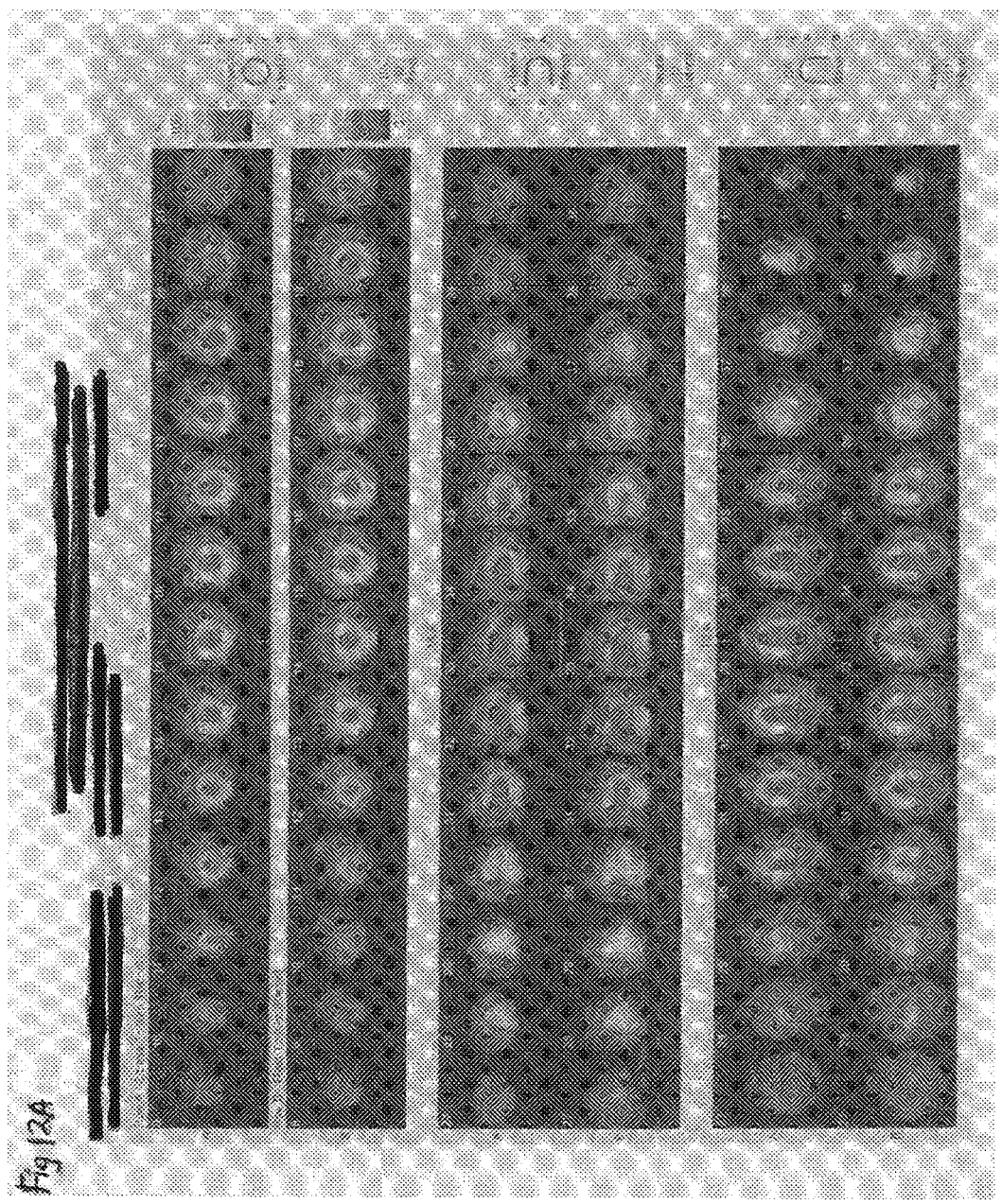
FIG. 12a shows results of conventional stress-rest imaging reporting coronary artery disease in both the left anterior descending (LAD) and obtuse marginal (OM) artery from the circumflex system.
Figure 12:
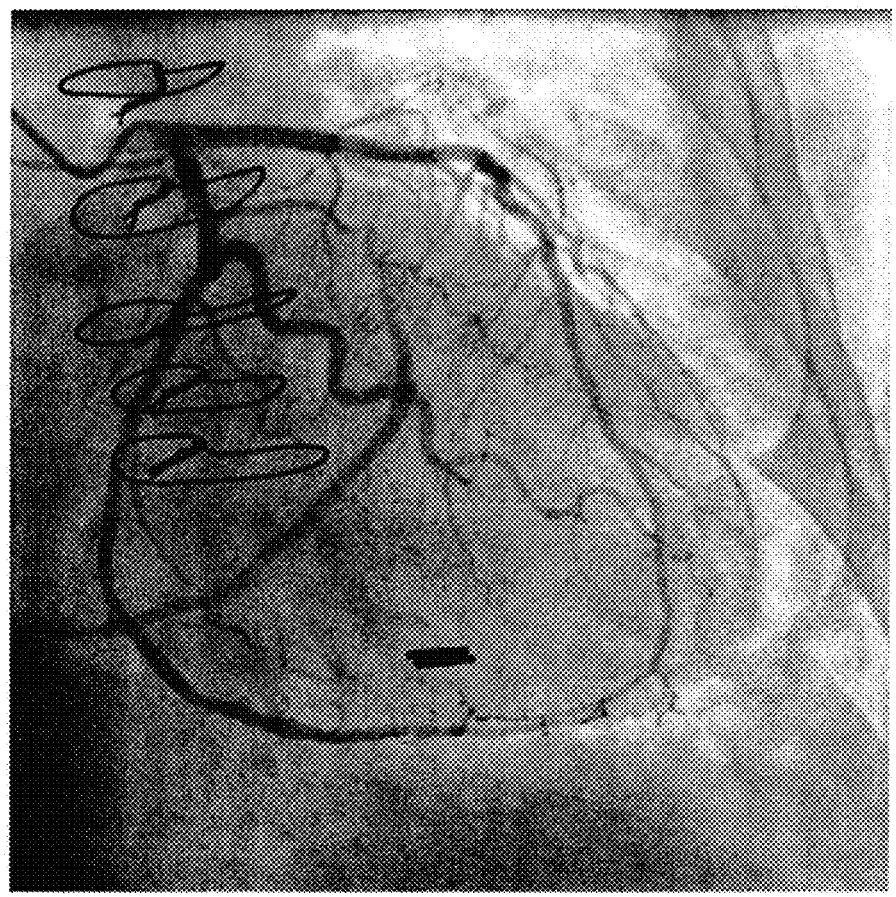
FIG. 12b shows the results of FHRWW© with a total cardiac "redistribution" of 5.7%, well within the expected isotope decay findings for a "normal" study without IVD.
FIG. 12c shows the results of coronary angiography, which agreed with FHRWW© revealing no IVD.

Identical ROIs are "quantified" for "emission" detection of isotope presence in the ROI as shown in FIG. 5. In addition to specific ROIs, including but not limited, to "total heart" and "total lung" (to define "heart to lung (H:L)" ratios), the basal anterolateral, mid anterolateral, basal inferoseptal, mid inferoseptal, basal anterior, mid anterior, basal infero-posterior and mid inferior" ROIs are determined as shown in FIGS. 5 and 12. The process is applicable on a pixel-by-pixel comparison of the five and sixty-minute results. The importance of H:L ratios has previously been defined for stress-rest images as described in Fleming R M, Feldmann K M. Comparing a High Dose Dipyridamole SPECT Imaging Protocol with Dobutamine and Exercise Stress Testing Protocols. Part II: Using High-Dose Dipyridamole to Determine Lung-to-Heart Ratios. Intern J Angiol 1998; 7:325-328; the disclosure of which is incorporated herein by this reference, but has not been investigated for "same state" conditions.

"Quantification" of FHRWW© is then performed through software, hardware, manual efforts or a combination of the these, following the steps laid out in appendix "A." Independent of whether software, hardware, manual efforts or a combination of these are used to accomplish this, the principles of the present invention are equally applicable and will be considered part of the present invention. When performed using our software, which carries out the present invention results, these results are then converted into a single image to prevent clinician error in interpretation of IVD findings. The importance of this cannot be overemphasized, just as MTF limits the ability to accurately quantify results of FHRWW© so to does Miller's Law (Visual Cognition Test) apply to the human capacity to integrate information. As demonstrated by this and the recent study on visual recognition by board certified radiologists from Brigham Women's Hospital, humans see what they believe is there and interpret what they see accordingly. The present invention single image may either provide raw data FHRWW© which may be applied to the algorithm (FIG. 7) for specific arterial regions to show "wash-in", "washout" or "normal" FHRWW© values or it may be provided by a color scale or black and white as desired. When performed manually, any software, hardware or manual efforts to produce a single image will be considered to be part of the principles of the present invention and will be considered to be under the patent of this present invention.

Identification of the thymus gland is made using either a visual inspection of the five-minute image to locate the thymus gland or abnormal tissue uptake, which may be located throughout the mediastinum as seen in FIG. 1b, or it may be noted by using computer analysis with the tracker ball, or similar application device depending upon the camera hardware and software, to identify areas of increased uptake.

Comparison of the results may be augmented by making certain that the images are "gated" as discussed in Fleming R M. Chapter 31. Nuclear Cardiology: Its Role in the Detection and Management of Coronary Artery Disease. *Textbook of Angiology*. John C. Chang Editor, Springer-Verlag New York, N.Y. 1999, pp. 397-406, the disclosure of which is incorporated herein by this reference. Such gated images may demonstrate regional wall motion abnormalities and left ventricular ejection fractions (LVEF) and should be done for comparison purposes for both the five and sixty-minute images post-stress to unmask regional and global ischemia as described by Fleming for "stress-rest" in Fleming R M. A Tate-en-Tate Comparison of Ejection Fraction and Regional Wall Motion Abnormalities as Measured by Echocardiography and Gated Sestamibi SPECT. Angiology 2002; 53:313-321; the disclosure of which is incorporated herein by this reference.

Figure 6:
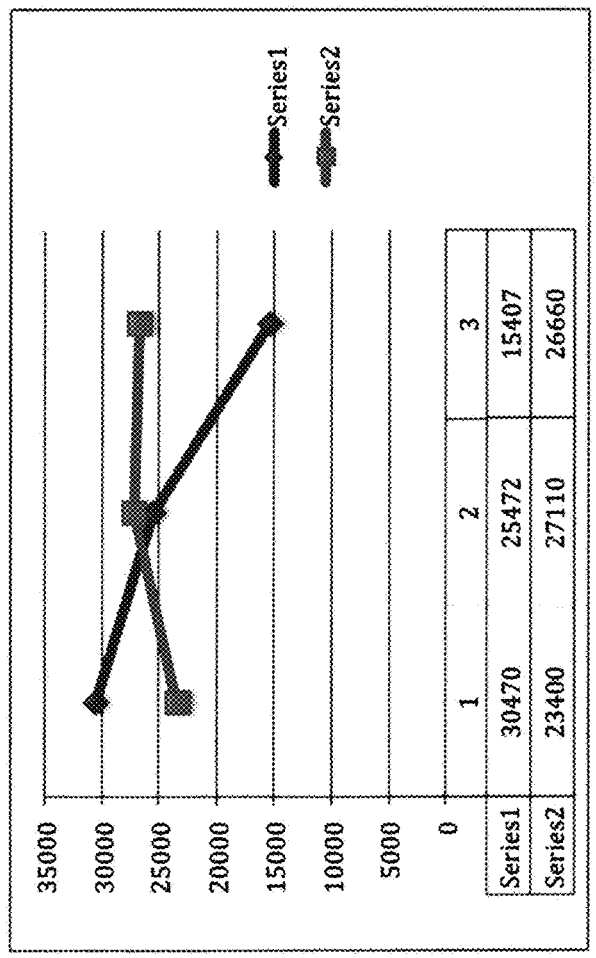
FIG. 6 shows a graphic comparison of what happens when scintillation emissions are "quantified" and compared to each other, demonstrating "wash-in", "washout" and "normal" coronary blood flow.

"Quantification" of FHRWW© for any given ROI, will demonstrate results revealing the presence of VIP ("wash-in"), IHD ("washout") or "normal" coronary flow)(SFR©) as seen in FIG. 6.

Each ROI may be viewed independently of the others or as a whole. When FHRWW© ROI values are determined, the parabolic relationship differentiating VIP and IHD for any given artery may be graphically visualized as a parabolic function as demonstrated in FIG. 7. Regions are matched to corresponding angiographic regions using the method already described by Fleming R M, Detecting Coronary Artery Disease Using SPECT Imaging: A Comparison of Thallium-201 and Teboroxime. Am J Physiol Imag 1992; 7(1):20-23; the disclosure of which is incorporated herein by this reference.

Figure 8:
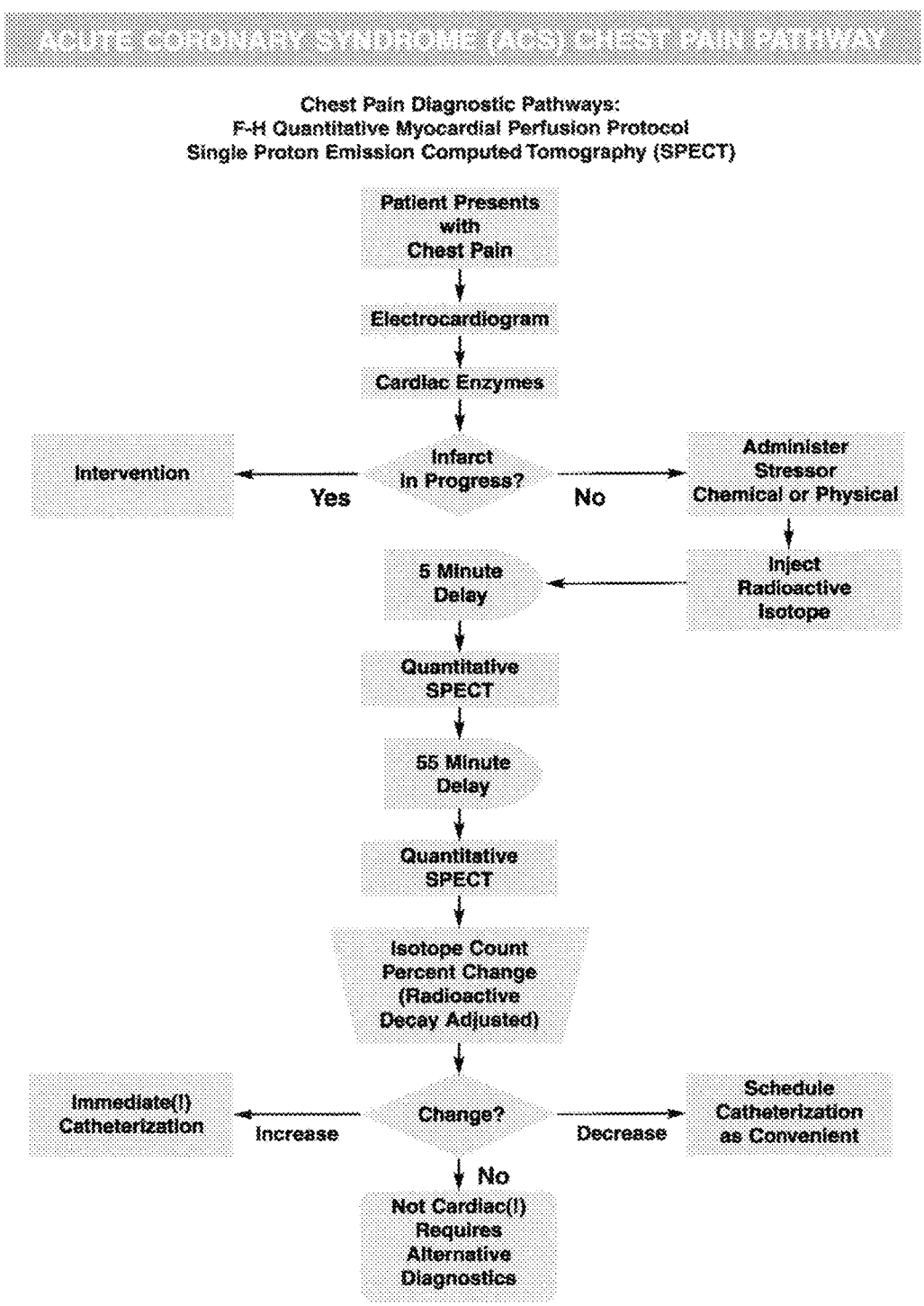
FIG. 8 shows an Acute Coronary Syndrome protocol for determining treatment regimen.

Patients presenting to emergency rooms with nuclear capability, may be evaluated using this method following the acquisition of images as described supra and following the algorithm defined by FIG. 8. The disclosure of this algorithm Fleming R M. The redistribution properties of Tc-99m isotope agents, sestamibi and myoview. Invited Presentation. Toronto International Pharmacy Conference, Toronto, Canada. Sept. 27-29, 2012, is incorporated herein by this reference.

The present invention additionally provides an improved method for the determination of tissue viability, differentiating "normal" cardiac tissue from "infarcted" tissue and further distinguishing between "stunned/hibernating" tissues, allowing for a significant clinical decision making process when deciding whether intervention of the IVD associated artery would be beneficial to the patient. As shown in FIG. 9, using the same steps for FHRWW© described in FIG. 4, minus the use of the "stressor" component of the protocol, FHRWW© (rest-rest) can be used to compare five and sixty-minute ROI "quantified" emissions to determine if the tissue is "normal", "stunned/hibernating" or "infarcted."

The invention is described in greater detail in the following non-limiting examples. While the present invention has been tested and described in connection with IVD and myocyte viability, the principles of the present invention are equally applicable to other organs of the body and are not limited to image acquisitions at five and sixty-minutes. Neither is it limited to the use of sestamibi. Any isotope, which is blood flow dependent, has a measureable half-life and can be quantified by current or future methods of isotope detection are applicable and defined by the principles of the present invention. Thus, it is neither intended nor should the present invention be interpreted as being limited to the detection of coronary artery disease and/or myocyte viability, the timing described, the use of sestamibi alone, nor the use of planar, SPECT, or PET cameras alone.

Examples

Following the discovery that sestamibi "redistributed" and that such "redistribution" could occur as early as five-minutes following venous introduction of the isotope under stress conditions (see FIG. 1), we investigated the "quantitative" characteristics of today's modern Geiger counters (viz. planar, SPECT and PET cameras). For our purposes, we specifically looked at MTF results of the two most common matrixes used for NCS, viz. the 64×64 and 128×128 matrix. Closed system (to prevent loss of isotope) samples of sestamibi were positioned one meter from the camera head of a Philips Forte Dual Head SPECT using a general all-purpose (GAP) collimator and a Picker Axis Dual Head SPECT camera using a low energy general all (LEGAR-PAR) purpose collimator with parallel hole positioning. Counts were acquired for five minutes and recorded and this process was repeated again fifty-five minutes later allowing for 10% isotope decay. This process was done using both the 64×64 and 128×128 matrix for each camera system.

The second part, included three hundred seventy-two (372) individuals ranging from 24 to 88 year of age who were studied using both the conventional stress-rest approach and FHRWW© approach using stress-stress imaging. Pharmacologic and physiologic stressors were used including adenosine, high-dose dipyridamole (HDD) defined as 0.852 mg dipyridamole/kg patient body weight, standard-dose dipyridamole (SDD) defined as 0.52 mg dipyridamole/kg patient body weight, lexiscan, dobutamine and treadmill stress using protocols described by Fleming R M. Chapter 31. Nuclear Cardiology: Its Role in the Detection and Management of Coronary Artery Disease. *Textbook of Angiology*. John C. Chang Editor, Springer-Verlag New York, N.Y. 1999, pp. 397-406; Fleming R M, Detecting Coronary Artery Disease Using SPECT Imaging: A Comparison of Thallium-201 and Teboroxime. Am J Physiol Imag 1992; 7(1):20-23; Fleming R M, Rose C H, Feldmann K M. Comparing a High Dose Dipyridamole SPECT Imaging Protocol with Dobutamine and Exercise Stress Testing Protocols. Angiology 1995; 46(7):547-556; Fleming R M, Feldmann K M. Comparing a High Dose Dipyridamole SPECT Imaging Protocol with Dobutamine and Exercise Stress Testing Protocols. Part II: Using High-Dose Dipyridamole to Determine Lung-to-Heart Ratios. Intern J Angiol 1998; 7:325-328; the disclosure of which is incorporated herein by this reference. There were no differences between the two groups based upon the use of "stressor." Additionally hs-CRP levels were measured, along with other markers of IVD; as described by Fleming R M. Chapter 64. The Pathogenesis of Vascular Disease. *Textbook of Angiology*. John C. Chang Editor, Springer-Verlag New York, N.Y. 1999, pp. 787-798; Fleming R M, Harrington G M. "What is the Relationship between Myocardial Perfusion Imaging and Coronary Artery Disease Risk Factors and Markers of Inflammation?" Angiology 2008; 59:16-25; the disclosure of which is incorporated herein by this reference. All subjects signed institutional consent forms prior to undergoing NCS.

Subjects were given either FDA approved doses of sestamibi or myoview for stress and rest images. The choice of agent depended upon physician preference and/or isotope availability. "Stress" doses ranged from 25-30 millicuries (mCi), with one-third of the respective "stress" dose, used for rest images. Stress doses were matched to within 2 mCi for the comparison of stress-rest and stress-stress (FHRWW©) studies. There were no differences between results obtained by either isotope.

Results were acquired, processed and reconstructed as described in Fleming R M. Chapter 31. Nuclear Cardiology: Its Role in the Detection and Management of Coronary Artery Disease. *Textbook of Angiology*. John C. Chang Editor, Springer-Verlag New York, N.Y. 1999, pp. 397-406, the disclosure of which is incorporated herein by this reference.

Figure 11:
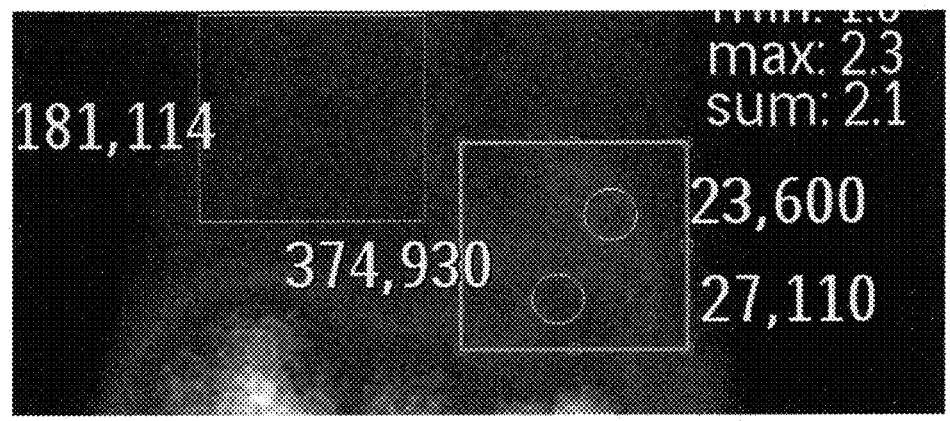
FIG. 11 shows "significant" left anterior coronary artery disease and left circumflex coronary artery disease as confirmed by coronary angiography, in the same patient shown in FIG. 9.
Figure 11:
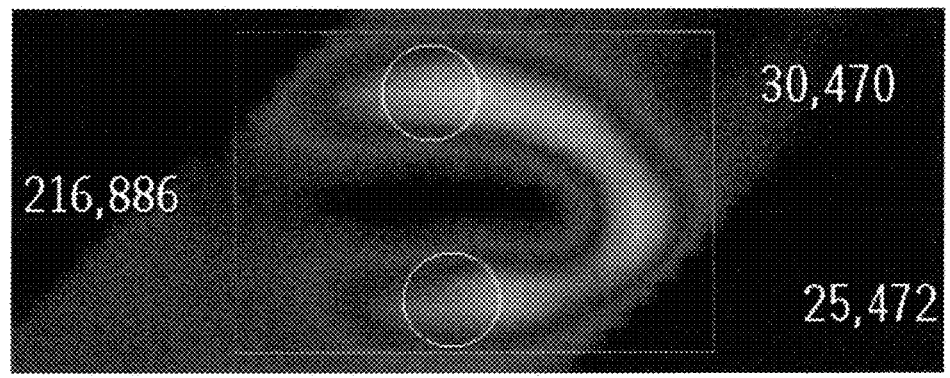
Figure 11:
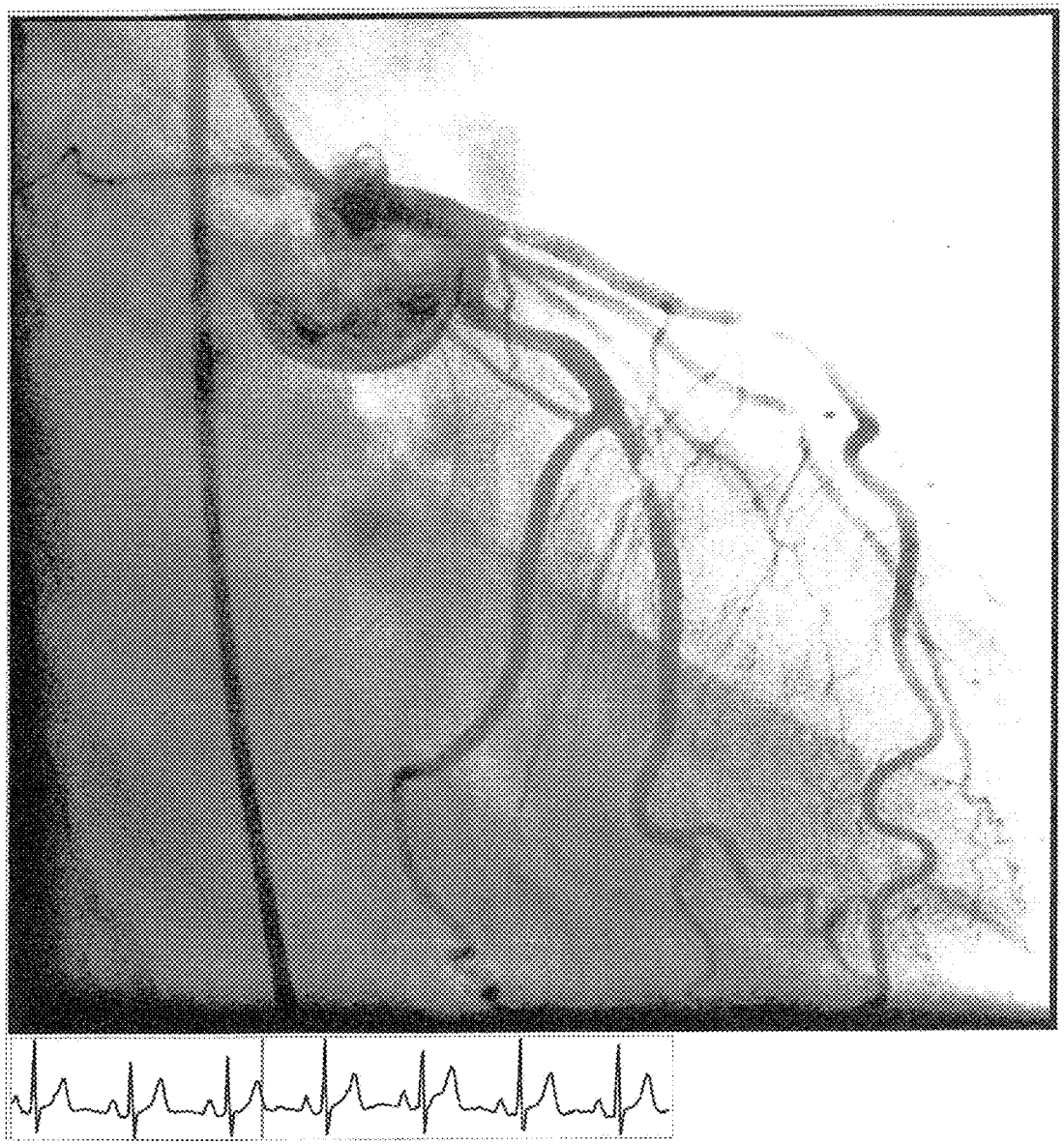

Display of NCS is made as described in Fleming R M. Chapter 31. Nuclear Cardiology: Its Role in the Detection and Management of Coronary Artery Disease. *Textbook of Angiology*. John C. Chang Editor, Springer-Verlag New York, N.Y. 1999, pp. 397-406, the disclosure of which is incorporated herein by this reference. An example of the conventional stress-rest image display is shown in FIGS. 10 and 12, while displays of FHRWW© are seen in FIGS. 11 and 12. Additionally, all five-minute images were displayed looking for evidence of thymus gland activation.

Comparisons of the NCS were made using coronary angiography including IVUS for further evaluation of VIPs in 85% of the cases as described supra to match arterial distribution with outcomes.

In the third part of this study, we looked at ten individuals to determine if tissue viability could be determined using rest-rest FHRWW© rest-rest comparisons. Individuals were given 8-10 mCi of sestamibi and imaged at five and sixty minutes post infusion of isotope, which was followed by a 10-20 cc normal saline flush to ensure adequacy of isotope delivery into the venous system for distribution.

Comparison of the Data and Statistical Analysis

Quantification of isotope emissions was accomplished using computer software provided by each camera company to be used with its specific hardware. The matrix was set at 64×64 to avoid MTF loss of data. Odds ratios (OR), correlation coefficients, mean±standard deviation, with 95% confidence intervals (CI) were determined. Two-tailed t-tests were used to determine significance between the two groups (stress-rest v. FHRWW©), using p-values of ≤0.05 to define statistical significance. All statistical analysis was determined using R-2.6.0 and GGobi software. Comparison of hs-CRP and IVD with associated thymus detection was also made.

The outcomes were compared with coronary angiographic and IVUS analysis of IVD using standard methods as previously defined by Fleming R M., Kirkeeide R L, Taegtmeyer H, Adyanthaya A, Cassidy D B, Goldstein R A. A Comparison of Technetium 99-m Teboroxime Tomography to Automated Quantitative Coronary Arteriography and Thallium—201 SPECT. J Am Coll. Cardiol. 1991; 17:1297-1302. Fleming R M., Kirkeeide R L, Smalling R W, Gould K L. Patterns in Visual Interpretation of Coronary Arteriograms as Detected by Quantitative Coronary Arteriography. J Am Coll. Cardiol. 1991; 18:945-951. Fleming R M, Gibbs H R, Swafford J. Using Quantitative Coronary Arteriography to Redefine SPECT Sensitivity and Specificity. Am J Physiol. Imag. 1992; 7:59-65. Fleming R M. Chapter 29. Atherosclerosis: Understanding the relationship between coronary artery disease and stenosis flow reserve. *Textbook of Angiology*. John C. Chang Editor, Springer-Verlag, New York, N.Y. 1999. pp. 381-387; the disclosure of which is incorporated herein as reference.

Study Results Part 1: Loss of Quantitative Ability Dependent Upon Modulation Transfer Function (MTF).

During the first part of the study, sealed syringes of Tc-99m sestamibi were fixed in position one meter from a Philips Forte Dual Head SPECT camera using a General All Purpose (GAP) collimator with heads positioned at 90 degrees. A 15% window was used with initially a 64×64 matrix and then a 128×128 matrix. Count acquisition data was obtained for each approach over 5 minutes duration at each step. We additionally conducted the same study using a Picker Axis Dual Head SPECT camera using a low energy general all (LEGAR-PAR) purpose collimator with parallel hole positioning. In this instance the camera heads were set to 102 degrees. The results of the Philips camera are shown in FIG. 2.

TABLE 1

Counts acquired using differing matrices resulting in loss of data due to modulation transfer function (MTF).

|  | Absolute Counts - 5 Minutes 64 × 64 Matrix | Absolute Counts - 60 Minutes 64 × 64 Matrix | Percentage Difference (Reduction) in Absolute Counts | Absolute Counts - 5 Minutes 128 × 128 Matrix | Absolute Counts - 60 Minutes 128 × 128 Matrix | Percentage Difference (Reduction) in Absolute Counts |
|---|---|---|---|---|---|---|
| Philips Camera | 1,405,721 | 1,251,359 | 10.98% | 3,473,001 | 2,966,394 | 14.59% |
| Picker Camera | 1,502,850 | 1,351,565 | 10.07% | 2,980,753 | 2,503,832 | 16.00% |

The results show a diminution in the ability of nuclear cameras to accurately measure isotope decay due to MTF loss of data as the matrix shifts from 64×64 to 128×128.

Accurate "quantification" of radioisotope emissions cannot be accurately measured due to MTF effect for a 128×128 matrix. The use of a 64×64 matrix under these conditions, provides an accurate method for employing the present invention.

Study Results Part 2. Comparison of the Present Invention with Conventional Stress-Rest (A.K.A. Rest-Stress) Imaging Compared with Coronary Angiographic Imaging.

The results of 372 patients (209 men, 163 women) ranging from age 24 to 88 (mean 51 years old), were studied using both conventional "stress-rest" or "rest-stress" approaches and compared with results of FHRWW© as described supra. Three hundred and twenty-seven (327) of these individuals underwent coronary angiographic and/or IVUS analysis. An example of one such patient is shown in FIGS. 10 and 11 and demonstrates the importance of using FHRWW© to both improve diagnostic accuracy, as well as save lives.

The results of LVEF and regional wall motion analysis provided additional information for both methods. While they improved diagnostic results included with final results in table 2, they did not statistically add to the accuracy. Therefore, they are recommended for additional clinical information, but did not significantly change final conclusions of the presence or absence of IVD.

Total heart to lung data was acquired for FHRWW© only and was useful for initial determination of overall IVD. As an initial evaluation, it proves to be quite useful as shown in FIG. 12. In this instance a woman presented for evaluation and given the findings of the "stress-rest" images, the physicians taking care of the patient elected to take the patient to coronary angiography (shown in FIG. 12), where she suffered a cardiac arrest, required placement of a temporary pacemaker, was placed on an intra-aortic balloon pump (IABP) in addition to pressor support. Fortunately, she recovered from the event; but suffered unnecessary renal damage (i.e. morbidity) as a result of clinicians following the "stress-rest" results, instead of the FHRWW© results.

Analysis of the initial five-minute images from FHRWW© with hs-CRP levels and detection of enhanced "thymus" gland uptake of sestamibi, showed an 8.6% incidence (32 of 372) of elevated hs-CRP levels, "thymus" identification and IVD.

The overall results of diagnostic accuracy for the two methods are shown in table 2. The odds ratio (OR) for "stress-rest" detection of IVD was 4.83 with a 95% confidence interval of 2.2 to 10.4 while FHRWW© had an OD of 57.0 (95% CI of 27.6 to 118.0) which was statistically significant ($p \leq 0.0001$) revealing FHRWW© superiority in detecting IVD. Of the false negatives using "stress-rest", approximately 18% had VIP on IVUS.

TABLE 2

Results of Diagnostic Imaging Detection of IVD.

| Test | Diagnosis | IVD by Angiography/ IVUS | No IVD by Angiography/ IVUS | Total Patients |
|---|---|---|---|---|
| Total with Coronary Angiography |  | 137 | 179 | 316 |
| Stress-Rest | IVD | 79 | 37 | 116 |
| Stress-Rest No | No IVD | 58 | 142 | 200 |
| FHRWW | IVD | 137 | 0 | 137 |
| FHRWW No | No IVD | 0 | 179 | 179 |

Figure 7:
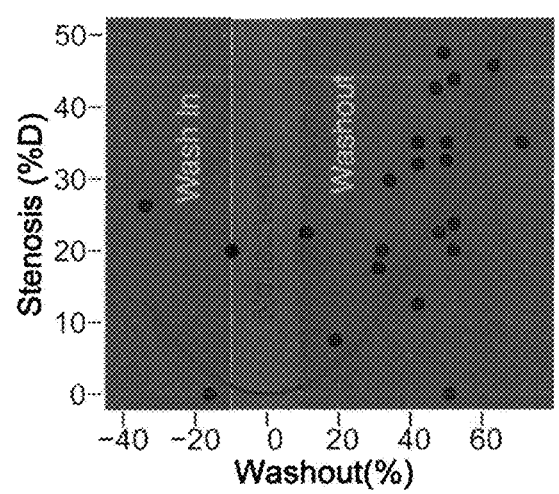
FIG. 7 shows the distribution of IVD differentiation between "wash-in" and "washout" phenomena as measured using FHRWW©.

While the results displayed reflect the use of "sensitivity" and "specificity" as generally used in the medical literature, a major distinction between the two methods (above and beyond diagnostic accuracy) is that "stress-rest" imaging is a YES/NO phenomena (hence, sensitivity and specificity), while FHRWW© is more diagnostically useful and represents a "quantitative" measurement of disease severity, which also allows for "quantitative" longitudinal measurement of treatment benefit as shown in FIG. 7. Here, FHRWW© correctly diagnosed the presence of "wash-in", "washout" and "normal" redistribution, and places these "quantified" results of the present invention in a parabolic relationship, distinguishing and differentiating 100% of the time IVD into IHD and VIPs.

This study demonstrated that FHRWW© was statistically superior to the "stress-rest" (or "rest-stress") approach for the detection and diagnosis of IVD. The present invention provides a "quantitative" method for both the detection of and the monitoring of treatment response to IVD. The addition of heart to lung ratios is of value for the initial evaluation of overall IVD. Comparison of "same state" results reveal that LVEF and wall motion abnormalities can be appreciated and clinically useful using the present invention. Furthermore, the ability to obtain immediate information from "thymus" detection while awaiting hs-CRP results, further guides clinical decisions in IVD. Finally, the use of FHRWW© allows differentiation of IHD from VIP and directs appropriate treatment decisions.

Further inspection of the present invention demonstrates that FHRWW© employing conventional imaging times and reduced imaging times, reveal several other advantages, including but not limited to reduced patient time in the nuclear laboratory for completion of patient component of the study (see FIG. 4) requiring less than one-quarter of the time for FHRWW© imaging. Additionally, there is a significant reduction in the amount of isotope required to perform the study, less staff and ancillary personnel exposure to patient associated radiation, reduced patient table time (FIG. 4), greater diagnostic accuracy reducing the need for additional testing and further radiation exposure and costs, decreased morbidity and mortality associated with FHRWW© accuracy. Notwithstanding the above, there are additional benefits including but not limited to further reductions in costs, time, isotope usage and exposure by combining the present invention with Breast Enhanced Scintigraphy Test©.

Part 3. Tissue Viability Using "Rest-Rest" FHRWW© Comparisons.

Ten individuals admitted for evaluation of IVD, additionally underwent evaluation of tissue viability using "rest-rest" FHRWW© as described supra. Comparisons of blood enzymes (troponin and CK levels), electrocardiograms and echocardiographic analysis of regional wall motion abnormalities were compared with FHRWW© evaluation of regional wall motion abnormalities on the "gated" NCS and the "quantification" of counts at 5 and 60-minutes following 25-30 mCi sestamibi injection, at rest.

Regional wall motion abnormalities consistent with tissue damage obtained from both echocardiographic and nuclear images matched in all ten cases. As shown in FIG. 9, regions which were not injured, showed greater uptake of sestamibi at 5-minutes (in blue), with a 25-30% loss of isotope (in green) fifty-five minutes later. Myocardial regions, which were "infarcted" electrocardiographically (demonstrating "transmural" infarction) showed initial counts almost identical to counts obtained at sixty minutes. Tissue which was not infarcted electrocardiographically but had enzyme changes (non-transmural) which demonstrated diminished regional wall motion both echocardiographically on and the nuclear images, showed diminished isotope uptake on the original five-minute study consistent with "normal" tissue, but greater than "infarcted" tissue. The follow up "same state" sixty-minute study showed similar "quantified" results as that of infarcted tissue; less than "normal" tissue.

"Rest-rest" FHRWW comparisons allow for tissue differentiation between "normal", "infarcted" and "stunned/hibernating" myocardium, which is diagnostically and clinically useful for determining potential benefit from treatment intervention.

It should be understood that various changes and modifications to the preferred embodiment described herein would be apparent to those skilled in the art. While the present invention has been tested in connection with the detection, diagnosis and treatment of IVD and cardiac tissue viability, the principles of the present invention are equally applicable to other organs and locations in the human body and also are equally applicable to other animal species. Such changes and modifications can be made without departing from the spirit and scope of the present invention and without diminishing its attendant advantages. It is therefore intended that such changes and modifications be covered by the appended claims.

What is claimed is:

1. A method of yielding quantitative diagnosis of bodily pathologies including vascular disease, metabolism and tissue differentiation in a subject comprising the steps of:
 a. either inject a pharmacologic agent or conduct physiologic changes, which produces regional blood flow differences;
 b. inject into the subject's body an isotope;
 c. after determining a time interval, with a computer, acquire one or multiple images at multiple time-points within the time-interval within a determined region of interest (ROI) within the patient;
 d. measure, with the computer, the actual measured radioactive emissions of the injected isotope from the acquired image or images;
 e. create, with the computer, a data array of radioactive emissions of the injected isotope at each time-point;
 f. calculate, with the computer, the total percent gain or loss of the measured radioactive emissions for the time period between each time-point of the data array set and the subsequent data array set;
 g. compare, with the computer, the calculated total percent gain or loss with the expected change resulting from the isotope radioactive decay;
 h. the degree of disease is determined, with the computer, in response to the comparison obtained in "g", this determined degree of disease is a non-linear function defined as the gain, washin, or loss, washout, which includes the differentiating of tissue and metabolism.

* * * * *